United States Patent
Albert et al.

(10) Patent No.: US 12,178,890 B2
(45) Date of Patent: Dec. 31, 2024

(54) METHOD TO DETECT BRAIN FUNCTIONAL ACTIVITIES USING HYPERPOLARIZED 129XE MR

(71) Applicant: LAKEHEAD UNIVERSITY, Thunder Bay (CA)

(72) Inventors: Mitchell Albert, Thunder Bay (CA); Francis Hane, Thunder Bay (CA); Yurii Shepelytskyi, Thunder Bay (CA); Tao Li, Thunder Bay (CA)

(73) Assignee: Lakehead University, Thunder Bay (CA)

( * ) Notice: Subject to any disclaimer, the term of this patent is extended or adjusted under 35 U.S.C. 154(b) by 120 days.

(21) Appl. No.: 16/747,221

(22) Filed: Jan. 20, 2020

(65) Prior Publication Data

US 2020/0268911 A1     Aug. 27, 2020

Related U.S. Application Data

(60) Provisional application No. 62/801,929, filed on Feb. 6, 2019.

(51) Int. Cl.
| | |
|---|---|
| *A61K 49/08* | (2006.01) |
| *A61B 5/00* | (2006.01) |
| *A61B 5/026* | (2006.01) |
| *G01R 33/56* | (2006.01) |
| *G01R 33/563* | (2006.01) |

(52) U.S. Cl.
CPC ............ *A61K 49/08* (2013.01); *A61B 5/0042* (2013.01); *A61B 5/0048* (2013.01); *A61B 5/0263* (2013.01); *G01R 33/5601* (2013.01); *G01R 33/56366* (2013.01)

(58) Field of Classification Search
CPC .... A61K 49/08; A61B 5/0042; A61B 5/0048; A61B 5/0263; G01R 33/5601; G01R 33/56366
See application file for complete search history.

(56) References Cited

U.S. PATENT DOCUMENTS

| | | | |
|---|---|---|---|
| 2008/0089846 A1* | 4/2008 | Driehuys | A61B 5/08 703/11 |
| 2012/0076378 A1 | 3/2012 | Keereman et al. | |
| 2018/0306882 A1* | 10/2018 | Li | G06V 10/774 |

OTHER PUBLICATIONS

Mazzanti, M., et al., "Distribution of Hyperpolarized Xenon in the Brain Following Sensory Stimulation: Preliminary MRI Findings," PLoS One. vol 6(7), 2011. p. 1-7 (Year: 2011).*
Chahal, S., et al., "Brain Imaging Using Hyperpolarized 129Xe Magnetic Resonance Imaging," Methods in Enzymology, Chapter Seventeen. vol 603, 2018. ISSN 0076-6879 (Year: 2018).*

(Continued)

*Primary Examiner* — Sean A Frith
(74) *Attorney, Agent, or Firm* — Michael R Williams; Ryan W Dupuis; Ade & Company Inc.

(57) ABSTRACT

Described herein is a method for detecting changes in blood flow in a tissue portion and/or body portion of an individual. The method can be used to detect any sort of pathology, trauma or insult which results in blood flow change. Specifically, this method uses hyperpolarized 129Xe MRI to detect xenon perfusion changes in tissues such as brain tissue that corresponds to changes in blood flow, for example, changes caused by functional activities of the brain or regions of the body where blood flow may be compromised.

5 Claims, 2 Drawing Sheets

(56) References Cited

OTHER PUBLICATIONS

Sharma, R., et al., "Physiological basis and image processing in functional magnetic resonance imaging: Neuronal and motor activity in brain," Biomedical Engineering Online. vol 3, 2004. p. 1-26 (Year: 2004).*
Amaro, E., et al., "Study Design in fMRI: Basic Principles," Brain and Cognition. 2006. p. 1-13 (Year: 2006).*
Kilian, W., et al., "Dynamic NMR Spectroscopy of Hyperpolarized 129Xe in Human Brain Analyzed by an Uptake Model," Magnetic Resonance in Medicine. 2004. p. 843-847 (Year: 2004).*
Ouriadov et al. "In Vivo Regional Ventilation Mapping Using Fluorinated Gas MRI with an X-centric FGRE Method," Preclinical and Clinical Imaging. vol 74, 2015. p. 550-557 (Year: 2015).*
Verma et al. "Overview of Dynamic Contrast-Enhanced MRI in Prostate Cancer Diagnosis and Management," Genitourinary Imaging. vol 198, 2012. p. 1277-1288 (Year: 2012).*
Swanson et al. "Brain MRI with Laser-Polarized 129Xe," MRM. vol 38, 1997. p. 695-698 (Year: 1997).*
Horn et al. "Multiple Breath Washout of Hyperpolarized 129Xe and 3He in Human Lungs With Three-Dimensional Balanced Steady-State Free-Precession Imaging," Magnetic Resonance in Medicine. vol 77, 2017. p. 2288-2295 (Year: 2017).*
Rao et al. "Imaging Human Brain Perfusion with Inhaled Hyperpolarized 129Xe MR Imaging," Radiology. vol 236(2), 2018. p. 659-665 (Year: 2018).*
Mazzanti, Mary L., et al., Distribution of Hyperpolarized Xenon in the Brain Following Sensory Stimulation: Preliminary MRI Findings, PLOS One, vol. 6, Issue 7, e21607, www.plosone.org.
Chahal, Simrun, et al., Brain Imaging Using Hyperpolarized 129Xe Magnetic Resonance Imaging, Elsevier Science & Technology, Methods in Enzymology, Chapter Seventeen, 2018, vol. 603, ISSN 0076-6879.
Hane, Francis T., et al., Inhaled Xenon Washout as a Biomarker of Alzheimer's Disease, MDPI, Diagnostics, 2018, 8, 41; doi: 10.3390/diagnostics8020041, www.mdpi.com/journal/diagnostics.
Fox, Matthew S., et al., Magnetic Resonance Imaging of the Brain Using Hyperpolarized 129Xe, The Royal Society of Chemistry, New Developments in NMR No. 4, Chapter 22, Apr. 13, 2015, www.rsc.org.
Rao, Madhwesha R., et al., Imaging Human Brain Perfusion with Inhaled Hyperpolarized 129Xe MR Imaging 1, Radiology: vol. 286, No. 2, Feb. 2018, radiology.rsna.org.

\* cited by examiner

METHOD TO DETECT BRAIN FUNCTIONAL ACTIVITIES USING HYPERPOLARIZED 129XE MR

PRIOR APPLICATION INFORMATION

The instant application claims the benefit of US Provisional Patent Application 62/801,929, filed Feb. 6, 2019 and entitled "A method to detect brain functional activities using hyperpolarized 129Xe MR", now abandoned, the entire contents of which are incorporated herein by reference for all purposes.

BACKGROUND OF THE INVENTION

Blood Oxygen Level Depend (BOLD) functional MRI detects the change of diamagnetic oxyhemoglobin to paramagnetic deoxyhemoglobin that takes place with brain activation and results in a decreased signal visible in MRI. While fMRI have demonstrated good correlation with PET and EEG, this technique requires sophisticated statistical analysis methods to interpret the results, due to the very small signal differences it captures.

Published US patent application 20160113501 provides a new acquisition scheme for T2-weighted BOLD fMRI. It employs a T2 preparation module to induce the BOLD contrast, followed by a single-shot 3D fast gradient echo (GRE) readout with short echo time (TE<2 ms). The separation of BOLD contrast generation from the readout substantially reduces the "dead time" due to long TE required in spin echo (SE) BOLD sequences. This approach termed "3D T2prep-GRE," can be implemented with any magnetic resonance imaging machine. This approach is expected to be useful for ultra-high field fMRI studies that require whole brain coverage, or focus on regions near air cavities. The concept of using T2 preparation to generate BOLD contrast can be combined with many other fast imaging sequences at any field strength.

Published PCT Application WO 2015070046 A1 teaches a system and method for analyzing blood flow in a subject's brain. In some aspects, the method includes analyzing fMRI data to identify signals related to blood flow, and selecting a zero time lag seed regressor using the identified signals. The method also includes correlating the selected seed regressor to identify a subset of the fMRI data that correlates with the seed regressor and is offset in time, combining the subset of the data to determine a time-delayed regressor, and performing repetitions to obtain a number of time-delayed regressors, where for each repetition, the seed regressor is adjusted using a previous time-delayed regressor. The method further includes analyzing the data using the time-delayed regressors to determine blood delivery from vessels across the brain, and generating a report. In some aspects, a second recursive procedure may be performed using an optimized seed regressor obtained from a first recursive procedure.

SUMMARY OF THE INVENTION

According to an aspect of the invention, there is provided a method for identifying a region of the brain activated by a stimulus comprising: administering a first quantity of hyperpolarized xenon gas to an individual; taking a control chemical shift image (either 2D or 3D) of the brain of the individual; measuring a chemical shift of xenon dissolved in blood of the individual; administering a second quantity of hyperpolarized xenon gas to the individual; subjecting the individual to a stimulus; taking a stimulus chemical shift image (either 2D or 3D); measuring a chemical shift of dissolved xenon in the blood of the individual; subtracting the stimulus chemical shift image from the control chemical shift image or subtracting the control stimulus image from the stimulus chemical shift image, thereby identifying the region of the brain of the individual activated by the stimulus. As discussed herein, this can also be done by calculating an effective spin-spin relaxation time constant instead of chemical shift to identify the activated regions.

As discussed herein, the hyperpolarized xenon gas can be administered to the individual by a variety of ways. For example, the individual may be ventilated with a mixture of hyperpolarized xenon gas and oxygen. In some embodiments, this ventilation may comprise having the individual breathe in hyperpolarized xenon gas, holding their breath for a short period of time, for example, approximately 20 seconds or for about 20 seconds or for at least 20 seconds, then expelling the hyperpolarized gas and respiring oxygen. It is of note that the oxygen respired may be air. As will be apparent to one of skill in the art, in these embodiments, a small amount of xenon may be used, for example, an amount that is approximately the same as the functional residual capacity of the lungs of the individual, that is, the volume of air left in the lungs after a normal breath out, or about 1-1.5 liters. in these techniques (~1 L). As discussed herein, in other embodiments, the hyperpolarized xenon gas may be administered by ventilating the individual with a mixture of at least 20% hyperpolarized xenon gas and oxygen, as discussed herein.

Additionally, the identification of the activated brain regions can be done using the same breathing protocol and acquiring either a time series of chemical shift images or a time series of gradient echo xenon images and then calculating a washout curve from the acquired images or scans. Due to the higher blood flow, the Xe signal will wash-out faster from regions of the brain which were activated by the stimulus, as discussed herein.

According to a further aspect of the invention, there is provided a method for determining blood flow to a region of interest comprising: while ventilating an individual with a mixture of oxygen gas and hyperpolarized xenon gas, (a) applying a pulse to a region of interest broad enough to saturate substantially all hyperpolarized xenon gas within the region of interest; (b) waiting for a first time interval; and (c) taking a first time interval magnetic imaging scan of the region of interest; and repeating steps (a)-(c) for at least a second time interval, wherein the second time interval is of a different duration than the first time interval.

DESCRIPTION OF THE PREFERRED EMBODIMENTS

Figure 1:
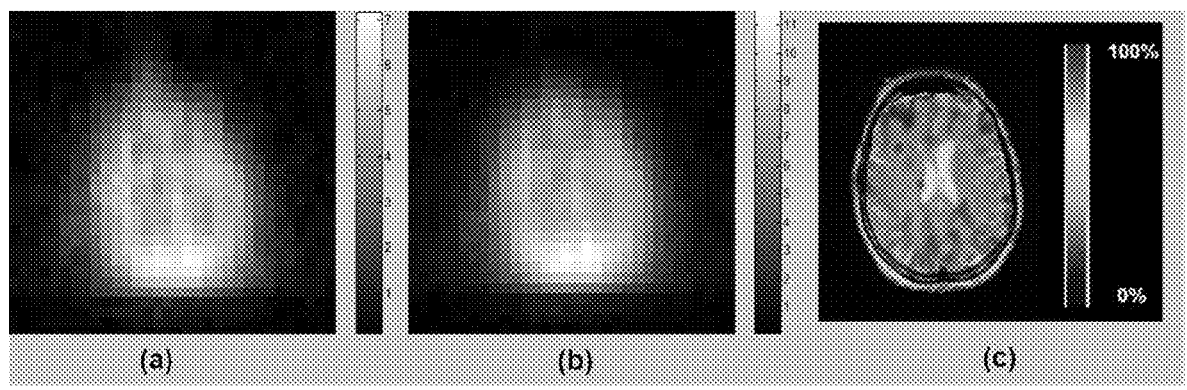
FIG. 1. (a) HP 129Xe MRI image of a human subject's brain at resting state, (b) HP 129Xe MRI image of the same subject under visual simulation, and (c) a calculated 129Xe signal enhancement map overlaid on top of proton MRI images of the brain, showing xenon signal increase at the back of the brain (visual cortex).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method for detecting changes in blood flow in a tissue portion and/or body portion of an individual. As will be appreciated by one of skill in the art, the method can be used to detect any sort of pathology, trauma or insult which results in blood flow change.

For example, blood flow can be compromised when a tissue portion is damaged, for example, damaged by exposure to fire, heat or extreme cold. Blood flow may also be compromised in tissue grafts or the like. Early detection of compromised blood flow allows the medical practitioner to intervene to try to prevent tissue necrosis; conversely, adequate blood flow indicates that intervention does not need to be taken and the tissue portion can be allowed to heal normally. Additionally, the narrowing of the blood-vessels (mostly arteries) due to a building up of plaques made from cholesterol, fatty substances, and cellular waste products can be detected by measuring of the intraarterial blood flow. As such, a decrease in blood flow can indicate plaque formation.

Similarly, in pathologies such as Alzheimer's disease, it is known that there is altered cerebral blood flow in AD subjects. Accordingly, a slower cerebral blood flow than observed in a control individual of similar age and condition for example general health condition may indicate that a subject has early stages of Alzheimer's disease.

Furthermore, it is well known that neuronal activities cause changes in local cerebral blood flow (CBF) and local blood volume. As discussed herein, by measuring changes in xenon perfusion, this can be used to map regions of the brain that are active when an individual is subjected to certain stimuli. Accordingly, the techniques described herein can be used for example to detect brain activity or brain disease, depending on how the scans are set up and the type of controls used, as discussed below.

While the method of the invention can be used to detect changes in blood flow in any tissue by measuring xenon perfusion, in some embodiments, changes in Cerebral Blood Flow (CBF) are detected. As discussed herein, it is of note that CBF changes in response to brain activities locally, depending on the types of stimulation, and can be mapped spatially, whereas pathologies such as most neurodegenerative diseases cause a globally altered CBF.

Specifically, this method uses hyperpolarized $^{129}$Xe MRI to detect xenon perfusion changes in brain tissue that correspond to changes in blood flow, for example, changes in CBF caused by functional activities of the brain.

Xenon, when inhaled into the lungs, can dissolve into the blood and be carried to and then dissolved into tissue by blood flow, for example, the brain tissues via CBF. Although chemically inert, xenon is biologically active and has long been used as a general anesthetic. Hyperpolarized (HP) Xenon MRI is an MR imaging technique that utilizes specially treated (hyperpolarized) xenon-129 gases as an imaging contrast to generate MR spectra and/or images of localized xenon perfusion in certain parts of human body.

For example, when a region of the brain is stimulated, it requires more oxygen as a result of exposure to the stimulus. However, the incoming level of oxygen can only be increased by increasing blood flow. When hyperpolarized Xe is also dissolved in the blood, a chemical shift of it and its relaxation parameters strongly depend on the chemical environment. For example, a higher amount of oxygen dissolved in blood leads to changes in the chemical environment for Xe which results in a different chemical shift and effective spin-spin relaxation time for Xe. Furthermore, by examining Xe wash-out from the brain, it is possible to determine the regions of a tissue for example the brain with higher blood flow because Xe will wash-out faster in these areas. By comparing a scan or image of the brain without stimulus for example prior to stimulus and a scan or image of the brain taken during or shortly after stimulus, there will be a different chemical shift, effective spin-spin relaxation time constant and faster wash-out of Xe in the stimulated area, whereas everywhere else these parameters should be approximately the same (+/− noise). Therefore, after subtraction, only the stimulated area of the brain appears on the scan. That is, the subtraction image is generated by comparing the stimulus image and the control image, for example, either by subtracting the stimulus image from the control image or the control image from the stimulus image, as discussed herein.

Thus, neuronal activities cause changes in local cerebral blood flow (CBF) and local blood volume, which in turn predominantly determine the amount of xenon that is transferred and dissolved into the brain tissue, as discussed herein. For example, by subtracting a baseline or control xenon MRI image of the brain from one taken when the subject is under stimulation (neuron activated), or by subtracting an MRI image of the brain taken when the subject is under stimulation (neuron activated) from a baseline or control MRI image of the brain, the difference in the xenon signals stands out as a reflection of the change in CBF, therefore indicating the region of the brain where the neural activity stimulated by the stimulus takes place.

According to an aspect of the invention, there is provided a method for identifying a region of the brain activated by a stimulus comprising:
   administering a first quantity of hyperpolarized xenon gas to an individual;
   taking a control magnetic resonance imaging scan of the brain of the individual;
   administering a second quantity of hyperpolarized xenon gas to the individual;
   subjecting the individual to a stimulus;
   taking a stimulus magnetic imaging scan of the brain of the individual; and
   generating a subtraction image of the brain by comparing the control magnetic resonance image of the brain and the stimulus magnetic resonance image of the brain, thereby identifying the region of the brain of the individual activated by the stimulus.

As discussed herein, the hyperpolarized xenon gas can be administered to the individual by a variety of ways. For example, the individual may be ventilated with a mixture of hyperpolarized xenon gas and oxygen. In some embodiments, this ventilation may comprise having the individual breathe in hyperpolarized xenon gas, holding their breath for a short period of time, for example, approximately 20 seconds or for about 20 seconds or for at least 20 seconds, then expelling the hyperpolarized gas and respiring oxygen. It is of note that the oxygen respired may be air. As will be apparent to one of skill in the art, in these embodiments, a small amount of xenon may be used, for example, an amount that is approximately the same as the functional residual capacity of the lungs of the individual, that is, the volume of air left in the lungs after a normal breath out, or about 1-1.5 liters. in these techniques (~1 L). As discussed herein, in other embodiments, the hyperpolarized xenon gas may be administered by ventilating the individual with a mixture of at least 20% hyperpolarized xenon gas and oxygen, as discussed herein.

According to an aspect of the invention, there is provided a method for identifying a region of the brain activated by a stimulus comprising:
  ventilating an individual with a mixture of oxygen gas and hyperpolarized xenon gas;
  taking a control magnetic resonance imaging scan of the brain of the individual;
  ventilating the individual with the mixture of oxygen gas and hyperpolarized xenon gas;
  subjecting the individual to a stimulus;
  taking a stimulus magnetic imaging scan of the brain of the individual; and
  generating a subtraction image of the brain by comparing the control magnetic resonance image of the brain and the stimulus magnetic resonance image of the brain, thereby identifying the region of the brain of the individual activated by the stimulus.

In some embodiments, the control magnetic resonance image of the brain and the stimulus magnetic resonance image of the brain are compared by subtracting the control magnetic resonance imaging scan from the stimulus magnetic imaging scan. In other embodiments, the control magnetic resonance image of the brain and the stimulus magnetic resonance image of the brain are compared by subtracting the stimulus magnetic resonance imaging scan of the brain from the control magnetic resonance imaging scan of the brain.

The stimulus may be for example but by no means limited to a visual stimulus, a motor stimulus or a pain stimulus.

In some embodiments, the mixture is no more than 80% xenon gas and no less than 20% oxygen gas. In other embodiments, the mixture is 70-80% xenon gas and 20-30% oxygen gas. However, as discussed above, in other embodiments, a quantity of hyperpolarized xenon gas corresponding approximately to the functional residual capacity of the lungs of the individual or about 1.0-1.5 liters is administered to the individual, that is, by having the individual breathe in or inhale a quantity of hyperpolarized xenon gas, as discussed herein.

Also described herein is another technique that can be used for the detection of the regional brain activity. As was described above, the brain stimulus causes a regional increase in blood oxygenation. As a result, the chemical environment of the dissolved hyperpolarized Xe in the stimulated region of the brain is different compared to the chemical environment in a region of the brain in an unstimulated or rest state. That is, the physical properties of dissolved Xe such as chemical shift, spin-lattice, and effective spin-spin relaxation times will be different. For example, increases in blood oxygenation results in a higher concentration of oxyhemoglobin, which is diamagnetic. Therefore, the effective spin-spin relaxation time of Xe will be longer in blood with higher levels of oxyhemoglobin.

In these embodiments, a chemical shift image (CSI) is acquired for both control and stimulated cases. Either a two-dimensional (2D) CSI or a three-dimensional (3D) CSI can be acquired. The CSI images can be converted into either a chemical shift map or an effective spin-spin relaxation map, for example, after mathematical calculations known to one of skill in the art. As discussed herein, these maps or the respective images or scans, can be used to identify the regions under increased or decreased oxygenation.

According to another aspect of the invention, there is provided a method for identifying a region of the brain activated by a stimulus comprising:
  administering a first quantity of hyperpolarized xenon gas to an individual;
  taking a control chemical shift imaging scan (2D or 3D) or a time series of CSIs or gradient echo Xe MRI scans of the brain of the individual;
  converting the acquired scan or image into a map of the dissolved Xe chemical shift, a map of the effective spin-spin relaxation of the dissolved Xe and/or recalculate the time series into the regional wash-out curves;
  administering a second quantity of hyperpolarized xenon gas to the individual;
  subjecting the individual to a stimulus;
  taking a stimulus chemical shift imaging scan of the brain of the individual (or a time series of CSIs or gradient echo Xe MRI scans);
  converting the acquired CSI image into the map of the dissolved Xe chemical shift and the effective spin-spin relaxation map of the dissolved Xe (or recalculate the time series into the regional wash-out curves); and
  subtracting the control chemical shift or relaxation maps or wash-out maps from the stimulus chemical shift or relaxation maps or wash-out maps respectively, thereby identifying the region of the brain of the individual activated by the stimulus.

According to an aspect of the invention, there is provided a method for identifying a region of the brain activated by a stimulus comprising:
  ventilating an individual with a mixture of oxygen gas and hyperpolarized xenon gas;
  taking a control chemical shift imaging scan (2D or 3D) or a time series of CSIs or gradient echo Xe MRI scans of the brain of the individual;
  converting the acquired scan or image into a map of the dissolved Xe chemical shift, a map of the effective spin-spin relaxation of the dissolved Xe and/or recalculate the time series into the regional wash-out curves;
  ventilating the individual with a mixture of oxygen gas and hyperpolarized xenon gas;
  subjecting the individual to a stimulus;
  taking a stimulus chemical shift imaging scan of the brain of the individual (or a time series of CSIs or gradient echo Xe MRI scans);
  converting the acquired CSI image into the map of the dissolved Xe chemical shift and the effective spin-spin relaxation map of the dissolved Xe (or recalculate the time series into the regional wash-out curves); and
  subtracting the control chemical shift or relaxation maps or wash-out maps from the stimulus chemical shift or relaxation maps or wash-out maps respectively, thereby identifying the region of the brain of the individual activated by the stimulus.

As will be appreciated by one of skill in the art, this method can be used by researchers to understand how the brain functions, as well as for clinicians to diagnose neurodegenerative diseases at early stages. Furthermore, this method is independent on the initial Xe amount.

As will be appreciated by one of skill in the art, it was previously demonstrated that areas of the brain of an individual with Alzheimer's disease did not diffuse Xenon gas as quickly as a control brain. However, this did not predict or suggest that activated regions of the brain could be detected using the method of the invention. Specifically, activated regions are associated with brain activities in response to external stimulation, which isn't necessarily different between healthy and AD brains. Furthermore, this aspect of the invention allows for investigation of specific region(s) of the brain, not just at the whole brain.

Specifically, mapping of the activation regions of the brain is important as changes in brain activity, for example, the region of the brain in which particular activities take place, may be correlated to early stages of different neurodegenerative disease.

Also described herein is another technique that can be used for the detection of blood flow changes in a portion of the body of an individual, for example, in a tissue portion in which blood flow may be compromised or to detect CBF change in a brain, which is referred to as Chemical Shift Saturation Recovery (CSSR) HP MRI.

After inhalation, $^{129}$Xe dissolves in blood and moves to the brain via the blood stream. Because the hyperpolarized (HP) state is in a non-thermally equilibrium state, the net magnetization cannot be recovered by a $T_1$ relaxation process. Consequently, prior to image acquisition, an additional pulse is applied. This pulse will destroy all hyperpolarization in the region of interest (ROI), for example, a tissue portion such as the brain or a region thereof. The saturation pulse should destroy hyperpolarisation during both stimulated and non-stimulated scans.

In these embodiments, a scan set is acquired with a different time delay between the saturation pulse and the image acquisition. As noted above, this can be done for both control and stimulated cases.

Specifically, a pulse is applied and after a specific time interval, an image is acquired. During this time interval, fresh HP xenon moves into the ROI and the SNR of the acquired image depends on the amount of the incoming Xe. By repeating the steps of applying a pulse and waiting for a specific interval before taking the next image while varying the interval or delay time, a recovery curve can be obtained. The recovery speed that is determined from the recovery curve is directly proportional to the blood flow. Specifically, the slope of the curve gives the information about the blood flow.

According to an aspect of the invention, there is provided a method for determining blood flow to a region of interest comprising:
administering hyperpolarized xenon gas to an individual,
(a) applying a pulse to a region of interest broad enough to saturate substantially all hyperpolarized xenon gas within the region of interest;
(b) waiting for a first time interval; and
(c) taking a first time interval magnetic imaging scan of the region of interest; and
repeating steps (a)-(c) for at least a second time interval, wherein the second time interval is of a different duration that the first time interval.

According to an aspect of the invention, there is provided a method for determining blood flow to a region of interest comprising:
while ventilating an individual with a mixture of oxygen gas and hyperpolarized xenon gas,
(a) applying a pulse to a region of interest broad enough to saturate substantially all hyperpolarized xenon gas within the region of interest;
(b) waiting for a first time interval; and
(c) taking a first time interval magnetic imaging scan of the region of interest;
(d) repeating steps (a)-(c) for at least a second time interval, wherein the second time interval is of a different duration that the first time interval. and generating a blood-flow or perfusion image by pixel-by-pixel analysis of the imaging scans acquired from steps (c) and (d)

In some embodiments, steps (a)-(c) are repeated for a third time interval. In other embodiments, steps (a)-(c) are repeated for a third time interval and for a fourth time interval. In yet other embodiments, steps (a)-(c) are repeated for a third time interval, a fourth time interval and a fifth time interval. As will be appreciated by one of skill in the art, the duration of each time interval is unique.

In some embodiments, the mixture is no more than 80% xenon gas and no less than 20% oxygen gas. In other embodiments, the mixture is 70-80% xenon gas and 20-30% oxygen gas. However, as discussed above, in other embodiments, a quantity of hyperpolarized xenon gas corresponding approximately to the functional residual capacity of the lungs of the individual or about 1.0-1.5 liters is administered to the individual, that is, by having the individual breathe in or inhale a quantity of hyperpolarized xenon gas, as discussed herein.

In some embodiments, the individual is subjected to a stimulus following the pulse but prior to taking the scan of the region of interest, as discussed above. In this way, the reaction to the stimulus across different time periods can be measured and/or determined.

The region of interest may be a tissue portion which is known to be, considered to be or is at risk of having blood flow thereto compromised.

Described herein is a method for detecting changes in blood flow in a tissue portion and/or body portion of an individual. As will be appreciated by one of skill in the art, the method can be used to detect any sort of pathology, trauma or insult which results in blood flow change.

For example, the tissue portion may be damaged, for example, damaged by exposure to fire, heat or extreme cold. Blood flow may also be compromised in tissue grafts or the like. Furthermore, the narrowing of the blood-vessels (mostly arteries) due to a building up of plaques made from cholesterol, fatty substances, and cellular waste products can be detected by measuring of the intraarterial blood flow. As such, a decrease in blood flow can indicate plaque formation.

As will be apparent to one of skill in the art, this time-interval based method is more sensitive than mapping. Mapping demonstrates the difference in local Xe concentration, and it is assumed that this difference caused mainly by perfusion change. However, using solely mapping and subtraction, there is the potential for some variability between scans due to a patient holding their breath, possibly requiring a mapping scan to be carried out more than once. As such, there is some potential for mapping to produce false-negative or false-positive results. On the contrary, the CSSR method measures blood-flow directly and it is independent of the initial Xe amount. It shows the speed of washing-in of Xe. Consequently, the effect of breath-holds on results will be minimal.

Accordingly, using this method, it is possible to detect blood-flow changes in different body parts, as discussed herein. It is further of note that any sort of stimulus will cause no affect on a blood-flow anywhere except brain.

As discussed herein, the described method can also be used for detection of brain activity and changes in brain activity; detection of Alzheimer's Disease based on perfusion; as well as detection of any disease or condition which results in blood-flow change.

As will be appreciated by one of skill in the art, it is also possible to use the recovery curve for diagnostics, as discussed herein or for example to test the success of medical interventions to improve blood flow, either mechanical or chemical, by taking a first recovery curve prior to intervention and then taking a second recovery curve post-intervention to determine what effect the intervention has had on the blood flow.

Figure 2A:
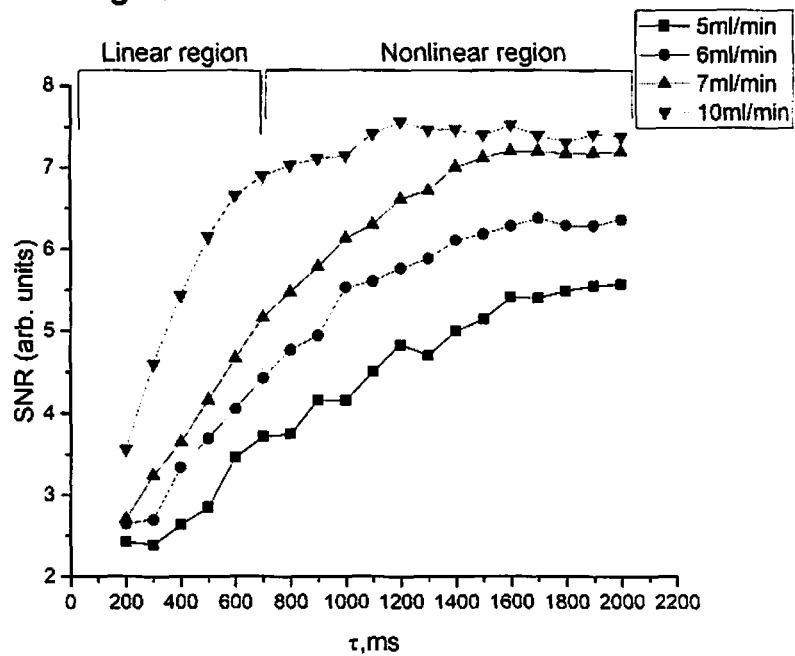
FIG. 2A. HP Xe CSSR curves obtained for the four different pump speeds of the pipe phantom.
Figure 2B:
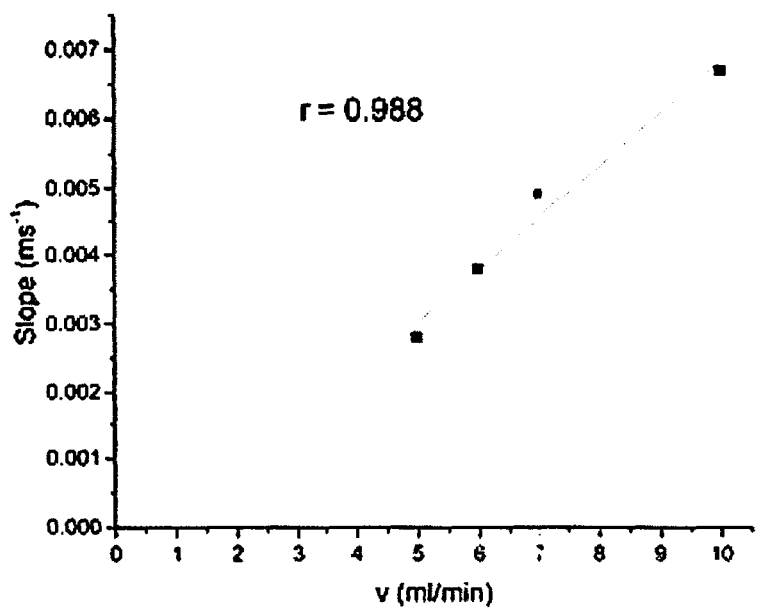
FIG. 2B. The quasilinear region between 200 ms and 700 ms was fitted using the linear equation and the correlation between the slope of the lines and the flow speed was calculated.

To demonstrate this aspect of the invention, a pipe having a small cross-section was connected to the syringe pump which worked in a constant flow regime. 30 ml of saline with dissolved HP Xe was pumped continuously and the CSSR experiment was conducted. FIG. 2 shows the recovery curves for the four following flow speeds: 5 ml/min, 6 ml/min, 7 ml/min and 10 ml/min. It could be clearly seen, that it is possible to detect the difference of 1 ml/min between two different flows. The two different areas can be seen on FIG. 2. The region of the short CSSR delays (from 200 ms to 700 ms) is quasilinear, whereas the nonlinearity was observed in the region of longer delays.

The linear area allows us to calculate the slope which correlates with a blood-flow. This area is the area of main contrast between different flows. Knowledge of the time region were the CSSR curve is linear can be used for example to set up scanning parameters properly.

The slope of the quasilinear region strongly correlates with a flow speed (Pearson's correlation coefficient r=0.988).

Compared to Blood Oxygen Level Dependent (BOLD) MRI, the signal to noise ratio of the maps generated from acquired images using this technique are substantially higher. Unlike BOLD fMRI which detects neuroactivities via the changes in deoxyhemoglobin concentration following stimulus, this technique detects the changes in the hemodynamic process (cerebral blood flow), which creates much higher contrasts, and therefore has an enhanced detection ability.

Compared to Electroencephalography (EEG), while EEG is superior in temporal resolution, EEG severely lacks spatial information for the detected signals, limiting its use to little more than global signal detection. This invention aims at overcoming these limitations of the existing techniques.

While the preferred embodiments of the invention have been described above, it will be recognized and understood that various modifications may be made therein, and the appended claims are intended to cover all such modifications which may fall within the spirit and scope of the invention.

REFERENCES

1. Albert M S, Cates G D, Driehuys B, et al.: Biological magnetic resonance imaging using laser-polarized 129Xe. Nature 1994:199-201.
2. Mary L. Mazzanti, Ronn P. Walvick, Xin Zhou, Yanping Sun, Niral Shah, Joey Mansour, Jessica Gereige, and Mitchell S. Albert, Distribution of Hyperpolarized Xenon in the Brain Following Sensory Stimulation: Preliminary MRI Findings, PLoS One. 2011; 6(7): e21607.
3. Madhwesha R. Rao, BEng, PhD, Neil J. Stewart, MPhys, PhD, Paul D. Griffiths, MBChB, PhD, FRCR, Graham Norquay, BSc, MSc, PhD, Jim M. Wild, MA, MSc, PhD Imaging Human Brain Perfusion with Inhaled Hyperpolarized 129Xe MR Imaging, Radiology, 162881-162881.
4. Rao M, Stewart N J, Norquay G, Griffiths P D, Wild J M: High resolution spectroscopy and chemical shift imaging of hyperpolarized 129Xe dissolved in the human brain in vivo at 1.5 tesla. Magn Reson Med 2016; 75:2227-2234.
5. Belliveau J W, Kennedy D J, McKinstry R C, et al. Functional mapping of the human visual cortex by magnetic resonance imaging. Science. 1991; 254:716.
6. Logothetis N K, Pauls J, Augath M, Trinath T, Oeltermann A: Neurophysiological investigation of the basis of the fMRI signal. Nature 2001; 412:150-157.
7. Singh M, Kim S, Kim T-S: Correlation between BOLD-fMRI and EEG signal changes in response to visual stimulus frequency in humans. Magn Reson Med 2003; 49:108-114.

The invention claimed is:

1. A method for identifying a region of the brain activated by a stimulus comprising:
    administering a first quantity of hyperpolarized xenon gas to a human individual while the human individual holds their breath;
    taking a control time series of gradient echo Xe MRI scans of the brain of the human individual;
    recalculating the control time series into control regional wash-out parameter maps;
    administering a second quantity of hyperpolarized xenon gas to the human individual;
    subjecting the human individual to a stimulus while the human individual holds their breath;
    taking a stimulus time series of gradient echo Xe MRI scans of the brain of the human individual;
    recalculating the stimulus time series into stimulus regional wash-out parameter maps; and
    subtracting the control regional wash-out parameter maps from the stimulus regional wash-out parameter maps, thereby identifying the region of the brain of the human individual activated by the stimulus.

2. The method according to claim 1 wherein the stimulus is a visual stimulus, a motor stimulus or a pain stimulus.

3. The method according to claim 1 wherein the hyperpolarized xenon gas is administered as a mixture of xenon gas and oxygen gas.

4. The method according to claim 3 wherein the mixture is 70-80% xenon gas and 20-30% oxygen gas.

5. The method according to claim 1 including applying a saturation pulse prior to acquisition of at least one scan of a time series.

* * * * *